(12) United States Patent
Karpowicz et al.

(10) Patent No.: US 7,485,112 B2
(45) Date of Patent: Feb. 3, 2009

(54) TUBE ATTACHMENT DEVICE FOR WOUND TREATMENT

(75) Inventors: John Karpowicz, Chester Springs, PA (US); Christopher L. Radle, Malvern, PA (US); Kevin P. Klock, Wynnewood, PA (US); John R. Boehringer, Wynnewood, PA (US)

(73) Assignee: Boehringer Technologies, L.P., Norristown, PA (US)

( * ) Notice: Subject to any disclaimer, the term of this patent is extended or adjusted under 35 U.S.C. 154(b) by 532 days.

(21) Appl. No.: 11/181,128

(22) Filed: Jul. 14, 2005

(65) Prior Publication Data

US 2006/0100586 A1    May 11, 2006

Related U.S. Application Data

(60) Provisional application No. 60/625,880, filed on Nov. 8, 2004.

(51) Int. Cl.
*A61F 13/00*     (2006.01)
(52) U.S. Cl. ..................................................... 604/304
(58) Field of Classification Search ................. 604/128, 604/129, 174, 176, 180, 268, 305, 313, 315–318, 604/327, 543; 602/41–43, 52
See application file for complete search history.

(56) References Cited

U.S. PATENT DOCUMENTS

| 1,385,346 A | 7/1921 | Taylor |
| 2,122,121 A | 6/1938 | Tillotson |
| 2,195,771 A | 4/1940 | Estler |
| 3,026,874 A | 3/1962 | Stevens |
| 3,367,332 A | 2/1968 | Groves ........................ 128/268 |
| 3,568,675 A | 3/1971 | Harvey |
| 3,874,387 A | 4/1975 | Barbieri |

(Continued)

FOREIGN PATENT DOCUMENTS

DE    2809828 A1    9/1978

(Continued)

OTHER PUBLICATIONS

M. E. Chariker, et al, "Effective Management of Incisional and Cutaneous Fistulae with Closed Suction Wound Drainage", *Contemporary Surgery*, vol. 34, Jun. 1989, pp. 59-63.

(Continued)

*Primary Examiner*—Kevin C Sirmons
*Assistant Examiner*—Bradley J Osinski
(74) *Attorney, Agent, or Firm*—Caesar, Rivise, Bernstein, Cohen & Pokotilow, Ltd.

(57) ABSTRACT

The invention provides a vacuum tube attachment device for vacuum assisted wound dressings. The device is in the form of a patch that can be attached to the primary wound cover. The patch forms a substantially air-tight seal to the primary wound cover, and a vacuum tube is fixed to the patch such that the patch can be oriented on the wound cover to locate the tube near an opening in the cover to allow vacuum pressure to be communicated to the wound. The patch has an adhesive area around its perimeter for attaching the patch in a substantially air-tight seal to the wound cover at any convenient location on the cover. Several embodiments of the patch are described.

9 Claims, 4 Drawing Sheets

U.S. PATENT DOCUMENTS

| | | |
|---|---|---|
| 4,382,441 A | 5/1983 | Svedman ............... 604/291 |
| 4,795,435 A | 1/1989 | Steer |
| 4,969,880 A | 11/1990 | Zamierowski |
| 5,100,396 A | 3/1992 | Zamierowski |
| 5,160,315 A | 11/1992 | Heinecke et al. |
| 5,261,893 A | 11/1993 | Zamierowski |
| 5,433,338 A | 7/1995 | Proshan |
| 5,527,293 A | 6/1996 | Zamierowski |
| 5,531,855 A | 7/1996 | Heinecke et al. |
| 5,549,584 A | 8/1996 | Gross |
| 5,891,077 A | 4/1999 | Gilman et al. |
| 6,071,267 A | 6/2000 | Zamierowski ............ 604/289 |
| 6,142,982 A | 11/2000 | Hunt et al. |
| 6,199,224 B1 | 3/2001 | Versland |
| 6,345,623 B1 | 2/2002 | Heaton et al. |
| 6,458,109 B1 * | 10/2002 | Henley et al. ............ 604/304 |
| 6,537,249 B2 * | 3/2003 | Kriesell et al. ............ 604/131 |
| 6,814,079 B2 | 11/2004 | Heaton et al. |
| 6,936,037 B2 | 8/2005 | Bubb et al. |
| 7,338,482 B2 | 3/2008 | Lockwood et al. |
| 2002/0016577 A1 | 2/2002 | Ohmstede |
| 2004/0064132 A1 | 4/2004 | Boehringer et al. |
| 2005/0101940 A1 | 5/2005 | Radl et al. |

FOREIGN PATENT DOCUMENTS

| | | |
|---|---|---|
| DE | 4012232 A1 | 10/1991 |
| GB | 1549756 | 8/1979 |
| GB | 2277035 A | 10/1994 |
| WO | WO03057071 A2 * | 7/2003 |

OTHER PUBLICATIONS

KCI, V.A.C. Freedom, "A Portable System for Advanced Wound Healing," 2004, Journal, 6 sheets.

US 6,216,701, 04/2001, Heaton et al. (withdrawn)

* cited by examiner

TUBE ATTACHMENT DEVICE FOR WOUND TREATMENT

REFERENCE TO RELATED APPLICATIONS

This application claims priority of U.S. Provisional Application No. 60/625,880, filed Nov. 8, 2004, entitled "TUBE ATTACHMENT COVER FOR VACUUM APPLICATION IN WOUND TREATMENT AND METHOD OF MANUFACTURING SAME".

FIELD OF THE INVENTION

The invention is related to the general field of wound treatment, and to the more specific field of devices for wound drainage and therapy by vacuum.

BACKGROUND OF THE INVENTION

It is well known to apply vacuum under air-tight wound covers in treating wounds. The vacuum can be used to suction wound exudate and other liquids from the wound and wound packing materials, and can be applied as a healing modality for its well known antiseptic and tissue regeneration effects.

The earliest devices for vacuum assisted wound therapy merely ran a tube, such as a Jackson Pratt hemovac drain or other similar tube with a ported distal end, under the edge of wound cover and applied an adhesive or paste around tube to maintain the air-tight seal. The other end of the tube was connectable to a pressure regulator of a hospital vacuum system, and sufficient negative pressure was applied to drain the wound and assist in healing. These devices reduced the frequency of dressing changes and the risk of infection as compared to conventional dressings. See, e.g., M. E. Chariker, et al, "Effective Management of Incisional and Cutaneous Fistulae with Closed Suction Wound Drainage", *Contemporary Surgery*, vol. 34, June 1989, pages 59-63. Other similar devices connected the end of a vacuum suction tube into a foam pad or other wound packing, and used a separate fluid supply tube for introducing medications or flushing fluid into the pad or wound packing. See, e.g. U.S. Pat. No. 4,382,441 (Svedman).

The adhesive seal around the vacuum tube or tubes which run under the edge of the wound cover in these prior wound dressings is vulnerable to cracking and breaching the air-tight seal created by the cover. Devices with more durable vacuum tube connections include using a tube with a flared or flanged distal end that can be fixed directly to the wound cover over a hole punched into the cover, as shown in U.S. Pat. No. 3,367,332 (Groves). U.S. Pat. No. 6,071,267 (Zamierowski) discloses a combination of these prior art devices in which a medication supply tube runs under the edge of the primary cover and a vacuum tube is connected into a foam pad located over a hole in the primary cover. U.S. Pat. No. 6,345,623 (Heaton) discloses another approach in which a suction head having a vacuum tube connector is placed on a foam pad in the wound, then a surgical drape with a hole in its center is placed over the suction head such that the connector protrudes up through the hole.

In their efforts to improve over these prior art devices, the present inventors considered several design objectives; including the objective of providing greater integrity to the seal between the primary wound cover and the skin, and determined that it would be preferable to locate the tube attachment on the outside of the primary wound cover rather than running the tube or tubes under the edge of the cover or through a slot or a seam in the cover. In addition to providing a more secure seal, locating the tube attachment on the outside of the primary wound cover allows the wound packing materials to be optimized to promote tissue growth and wound healing, since the packing materials do not need to provide support or connection for the tubes.

Locating the vacuum tube attachment on the outside of the primary wound cover can be accomplished by a tube that is integrally attached to the primary cover and that has a sidewall port located over a hole in the primary cover, as shown in published application US 20040064132. However, another design consideration for the present invention was that it would be an advantage over prior vacuum dressings to provide the tube attachment in the form of a patch that can be applied to a primary wound cover, rather than as an integral part of the outer surface of the cover. This feature allows the same patch to be used with primary wound dressing covers of different sizes and shapes, and allows the caregiver to locate the patch in the most convenient location over the wound, as opposed to using an integral device in which the tube is attached over a hole at a fixed location on the primary cover. As an additional advantage, the same patch can be detached and reused on a new primary cover when the dressing is changed, and in the rare event of a patch needing to be replaced, it can be replaced without removing the primary cover from the wound.

In the course of developing a vacuum assisted wound system using a tube attachment patch, the inventors discovered that the patch can be used by itself to provide a vacuum applicator over small wounds. Although not a primary objective, this alternative use should be considered an additional aspect of the invention.

These and other advantages and aspects of the invention will become apparent upon reading the detailed description and drawings which follow.

BRIEF SUMMARY OF THE INVENTION

In the aspect of the invention relating to the vacuum tube attachment for a vacuum assisted wound dressing, the invention provides an attachment device in the form of a patch that can be attached to the primary wound cover. The patch forms a substantially air-tight seal to the primary wound cover, and a vacuum tube is fixed to the patch such that the patch can be oriented on the wound cover to locate the tube near an opening in the cover to allow vacuum pressure to be communicated to the wound. The patch has an adhesive area around its perimeter for attaching the patch in a substantially air-tight seal to the wound cover at any convenient location on the cover. The caregiver merely cuts an opening in the cover and applies the patch over the opening such the patch supports the tube near the opening.

In one embodiment, the patch has fixed to it a frame holding the vacuum tube, or holding a plurality of tubes including the vacuum tube. In a preferred version of this embodiment, there are two tubes in a spaced parallel relationship in the frame, and the patch may be applied to the primary cover with the opening located between the tubes. The second tube may be used for monitoring pressure in the system or monitoring some other parameter of the dressing or wound, or it may be used to supply medication or flushing fluids to the wound. The frame may also be formed as an enclosure that creates an effective suction chamber around a ported portion of the tube or tubes. The patch includes a transparent thin film bonded to the sides of the frame which extends outward from the frame and has adhesive material applied to it at the perimeter of the patch.

The vacuum tube preferably has a portion at or near the distal end which has a plurality of circumferential flanges, and has ports located in the troughs between adjacent flanges. The invention will work if the flanges are partial and only extend over a bottom portion of the circumference. The flanges prevent the primary wound cover from being drawn against or into the ports and blocking them.

In another embodiment, the patch is a sheet of flexible material having a thickness substantially greater than the thickness of the primary wound cover. An aperture is cut into in the sheet, and a vacuum tube having a port in its side wall is attached to the sheet over the aperture, in an orientation such that the portion of the tube over the aperture lies substantially parallel to the sheet and the port is substantially in register with the aperture. The patch has an adhesive area around its perimeter for attaching the patch in a substantially air-tight seal to the wound cover at any convenient location on the primary cover.

In the aspect of the invention relating to vacuum assisted wound dressings, the tube attachment devices may be used in combination with a primary wound cover, or applied directly to the skin surrounding smaller wounds.

DESCRIPTION OF THE INVENTION

Figure 1A:
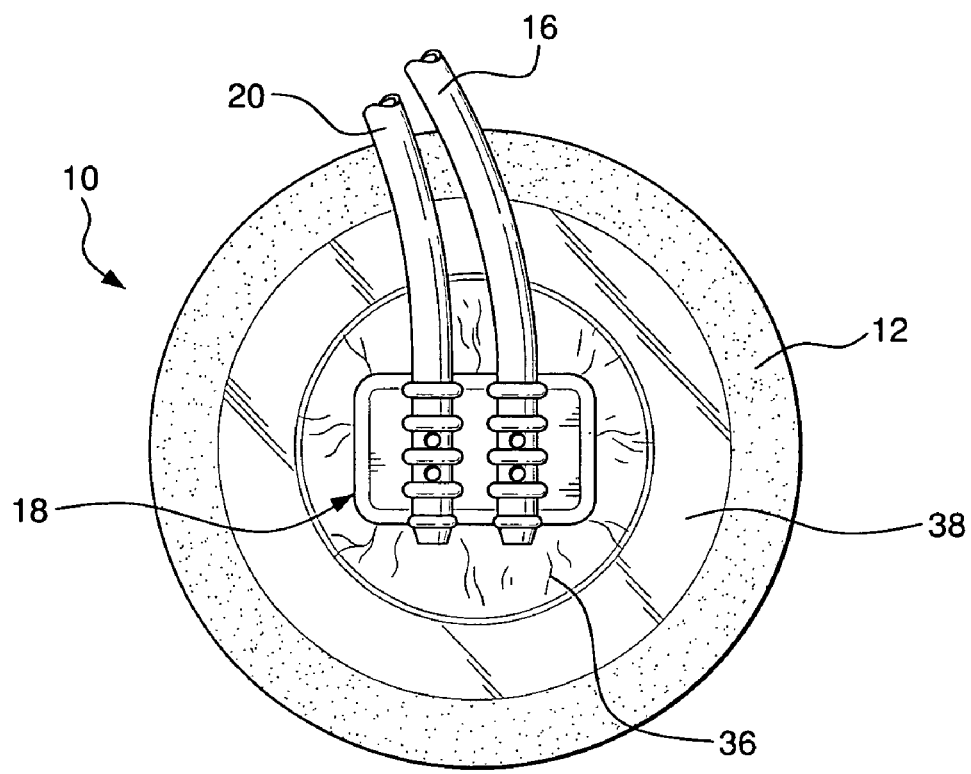
FIG. 1A is a bottom view of one embodiment of a vacuum tube attachment patch.

In the drawings and description which follow, a device for attaching a vacuum tube to a vacuum assisted wound dressing is shown in embodiments in which the device is a tube attachment patch that can be adhered to the outer surface of a sealed wound cover in any one of various locations on the cover. Thus, a thin-film wound dressing of a standard size or shape can be applied in a substantially air-tight seal to the skin surrounding a wound without regard to locating a fixed tube connector over the wound, or to creating a seam between sheets of film through which to pass a tube. Instead, the film dressing can be applied as the primary wound cover in an orientation suited for patient comfort and the integrity of the air-tight seal, following which a small air opening can be cut in the cover and the tube attachment patch applied over the opening to maintain the overall vacuum seal. Several embodiments of a tube attachment patch, not intended to be exhaustive or limiting, are described herein.

Figure 1B:
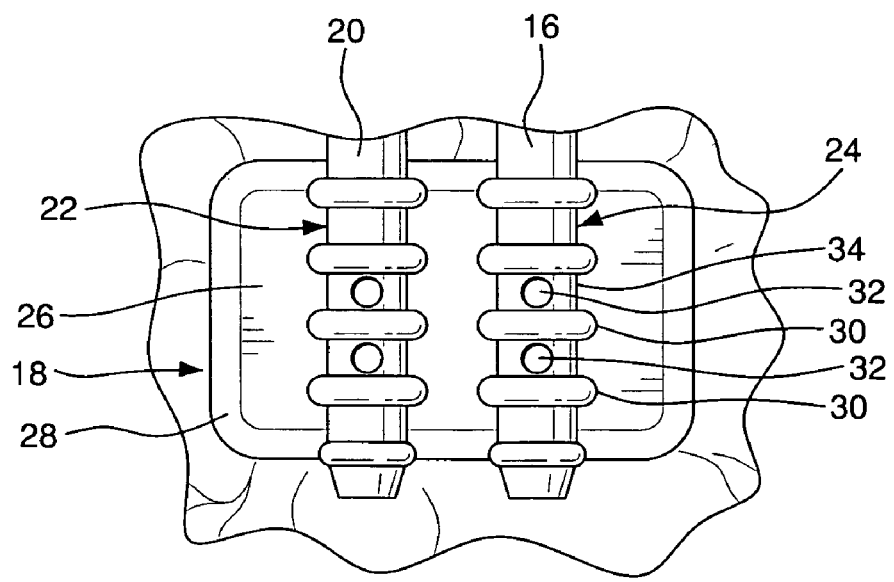
FIG. 1B is a close-up view of the tube attachment frame and tubes shown in FIG. 1A.
Figure 2:
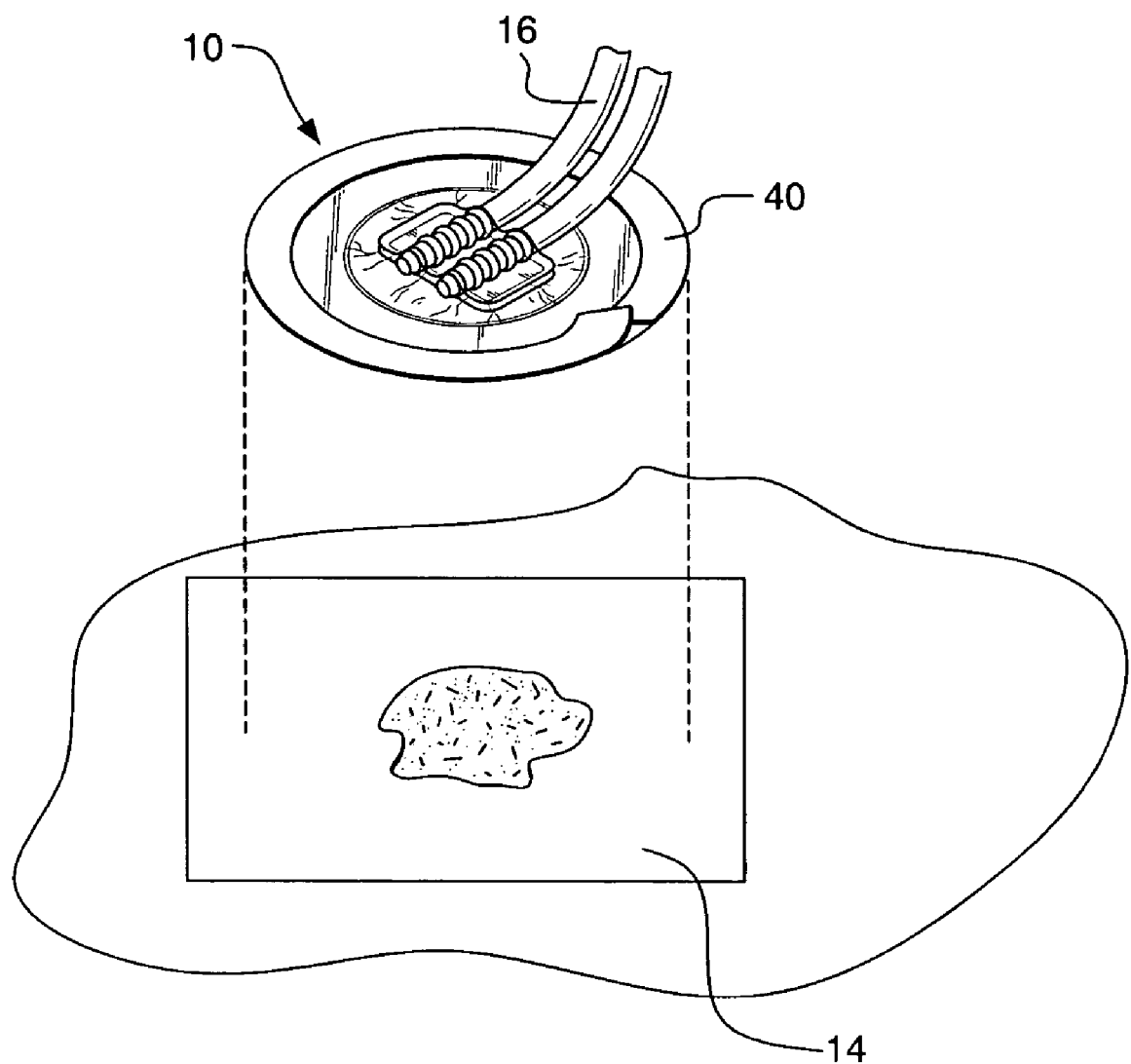
FIG. 2 is a view of a vacuum assisted wound dressing in which a patch of the embodiment shown in FIG. 1 is shown spaced apart from a primary wound cover over a wound.

The embodiment of tube attachment patch 10 shown in FIGS. 1A and 1B, has an adhesive material 12 applied around its perimeter to attach the patch in a substantially air-tight seal to a primary wound cover (shown as 14 in FIG. 2). A vacuum tube 16 is fixed to the patch such that the patch can be oriented on the wound cover to locate the tube near an opening (not shown) made in the cover to allow vacuum pressure to be communicated to the wound. In the preferred embodiment shown in FIGS. 1 and 2, the tube attachment patch 10 includes a frame 18 holding the vacuum tube 16.

Although a single tube to apply the vacuum pressure is sufficient for a vacuum assisted wound dressing, the frame 18 may also hold a second tube 20 in spaced parallel relation to the vacuum tube 16, whereby the patch 10 can be oriented on the wound cover 14 such that the opening (not shown) made in the cover is positioned between the two tubes 16, 20. The second tube 20 may be adapted for monitoring the operation of the vacuum assisted wound dressing, such as sensing excessive air flow as an indication of a leak in or around the wound cover. Alternatively, the second tube may be extended beyond the vacuum tube such that the second tube can be inserted through the opening made in the wound cover to the wound packing and used to deliver liquids to more effectively flush the wound or apply medication. Another alternative is that the vacuum tube 16 could be a coaxial tube with two lumens (not shown), one lumen for applying the vacuum pressure and the other for monitoring the operation of the wound dressing or delivering fluids.

The frame 18 is merely a robust structure of the patch to which the tube or tubes are physically connected, rather than connecting them to the thin film material of the patch. A simple frame can be made, for example, by heat welding a piece of relatively thick plastic, such as ten mil thickness urethane, to the top surface of the tube or tubes, and then heat welding the edges of the thick urethane piece to the thin film of the patch. 10. In an embodiment as shown in FIGS. 1A and 1B, however, the frame 18 is an enclosure that can create an effective suction chamber around a ported portion 22 of the vacuum tube 16; and if a second tube is used in the manner shown in FIGS. 1 and 2, around a ported portion 24 of the second tube 20. Although the frame 18 depicted in FIGS. 1 and 2 has a rectangular shape, other shapes can be used and still create an effective suction chamber around the tubes. A suction chamber is formed because the frame 18 has a main body 26 to which the vacuum tube(s) are connected, such as by heat welding, and a flexible skirt 28 depending downward from the main body to provide a conforming air tight seal between the skirt and wound cover.

A portion of the vacuum tube 16 within the area formed by the frame 18 has a plurality circumferential flanges 30, and has vacuum communication ports 32 located in the troughs 34 between adjacent flanges. The second tube 20 may have a similar configuration. Although two ports are shown in each tube in the embodiment of FIG. 1, it is only necessary to have at least one port. Locating a port in a trough between adjacent flanges helps prevent the vacuum pressure from pulling the wound cover up against or into the port and cutting-off the vacuum communication to the wound.

The patch of FIG. 1 further includes section of relatively thin film, such as 1 mil thickness urethane, bonded to the sides of the frame and extending outward toward the perimeter of the patch. This film 36 may be continued all the way to the perimeter, but in the embodiment of FIG. 1A, a transparent film 38 having the same or similar transparency as the primary wound cover is welded to the urethane film 36 and extends to the perimeter of the patch. Matching material to the primary wound cover will allow the wound to be inspected without removing the dressing. For example, if the primary cover is a Tegaderm® dressing, the transparent film portion 38 of the patch may also be formed of Tegarderm® film that is heat welded or otherwise bonded to the urethane film 36. Alternatively, the Tegarderm® film could be bonded directly to the frame 18. It is also preferred that when the primary cover is a film having sufficient permeability to maintain a vacuum around the wound while permitting ingress of oxygen and egress of water vapor through the film, the transparent thin film portion 38 of the patch should have the same or similar permeability.

The adhesive material 12 may be applied to the underside of the film 38 around the perimeter of the patch to effect an air tight adherence to the primary cover. Preferably the adhesive material is a pressure release adhesive having a release force sufficient to maintain the air tight seal, but low enough to allow the patch 10 to be removed and reapplied to the same cover, or to a new cover, during dressing changes.

As shown in FIG. 2, the patch 10 can be applied at any orientation to a primary wound cover 14 that has been attached to the skin in an air-tight seal over a wound. Normally a wound packing material (not shown) is placed into the wound channel before the primary cover is attached to the skin. Then the caregiver can cut a small hole into the primary cover at a location she or he selects for patient comfort and apply the patch such that the ported section of the vacuum tube is next to the hole in the cover.

Figure 3:
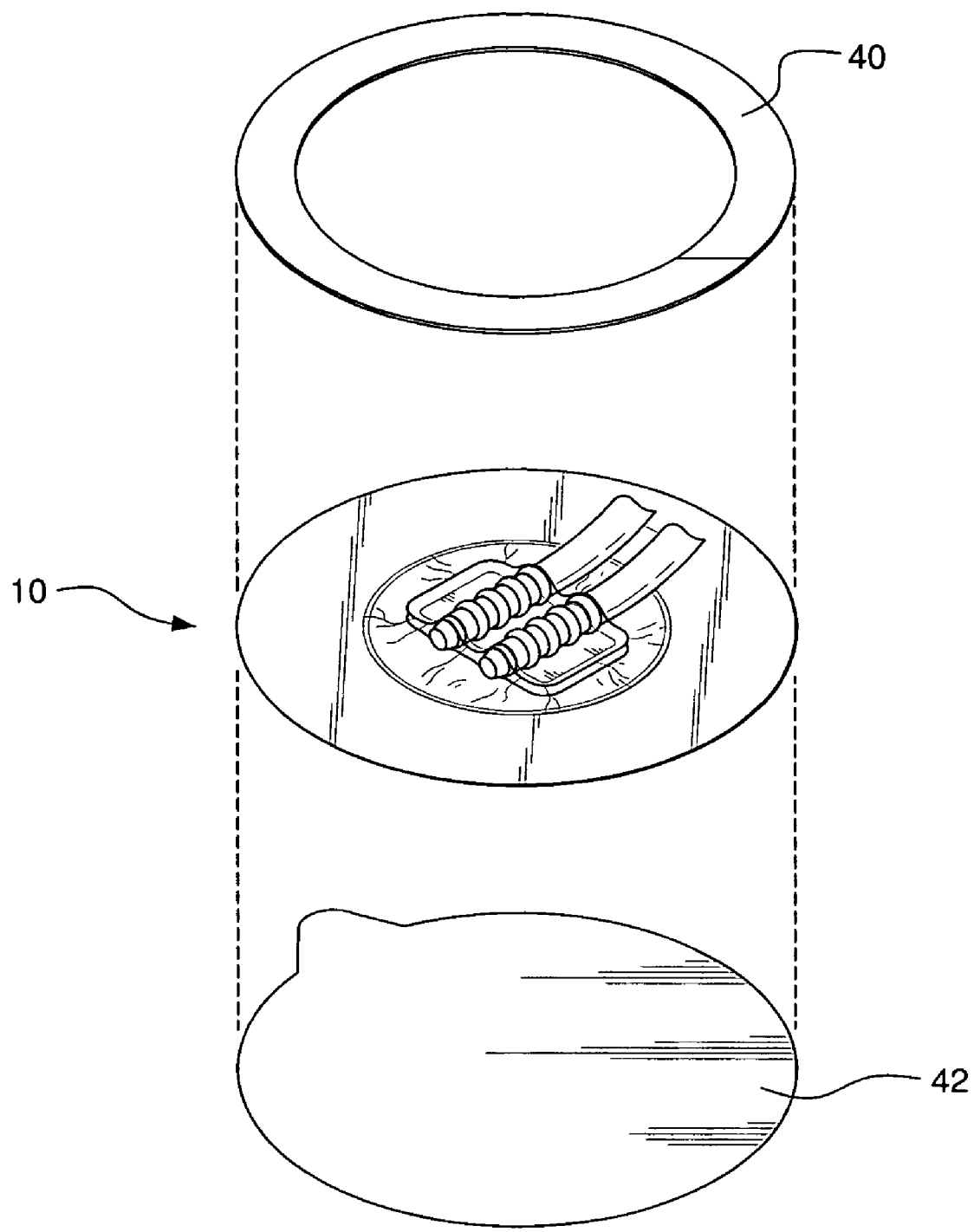
FIG. 3 is a view of the patch of FIGS. 1 and 2 showing the peel-off cover and collar which are applied to the patch for handling and removed at the time of application.

For convenience in handling, shipping and application, the patch 10 as shown in FIG. 3 may be supplied with a peel-off cover 42 of suitable backing material, such as stiff paper or plastic, adhered to and covering the side of the patch on which the adhesive material 12 is applied. This peel-off cover maintains the shape of the patch and prevents the adhesive from adhering to surrounding objects or packaging until the patch it is ready to be applied to the primary cover. The patch may also have a peel-off collar 40 of suitable backing material, such as polymer foam, applied in an annular strip around the perimeter of the opposite side of the patch. The collar holds the shape of the patch and provides a press area to press down upon the patch over the adhesive material to make an air tight seal with the primary wound cover. The collar 40 may be peeled away after the patch is set on the cover.

Figure 4A:
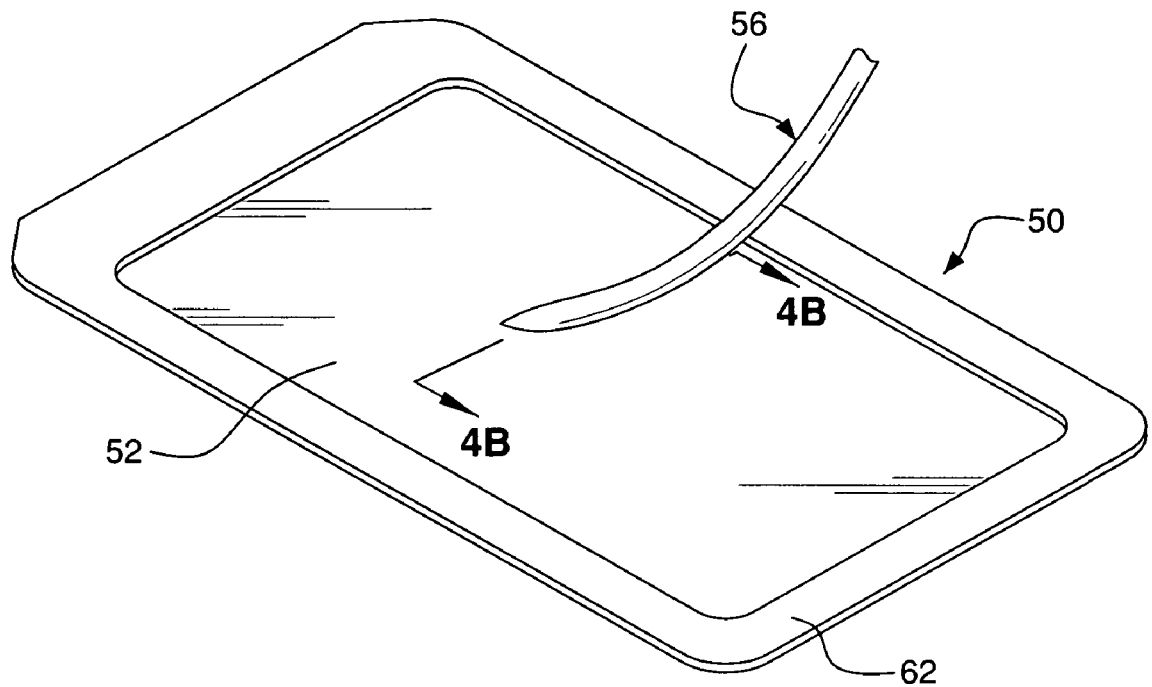
FIG. 4A is a perspective view of a second embodiment of tube attachment patch.
Figure 4B:
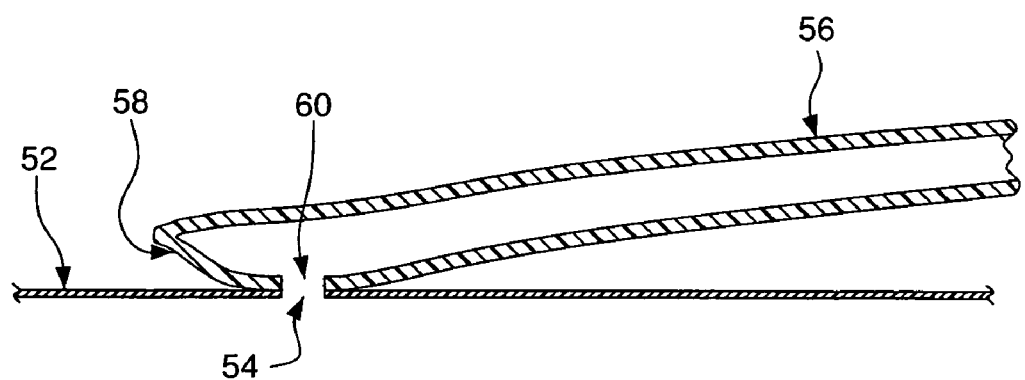
FIG. 4B is a cross section view of the patch of FIG. 4A.

In a second embodiment shown in FIGS. 4*a* and 4*b*, a patch 50 is formed with a sheet of flexible material 52, such as a thermoplastic elastomer, having a thickness greater than the thickness of the primary wound cover. An aperture 54 is formed in the sheet. A vacuum tube 56 is provided with a closed end 58 and a port 60 in its side wall. The tube 56 is attached to the sheet 52 over the aperture 54 in an orientation such that the portion of the tube over the aperture lies substantially parallel to the sheet and the port 60 is substantially in register with the aperture 54. This orientation allows the tube to lie essentially flat along the primary cover instead of sticking up from it. The patch has an adhesive area (not shown) around its perimeter for attaching the patch in a substantially air-tight seal to the wound cover at any convenient location on the primary. As shown in FIG. 4A, a peel-off collar 62 of suitable backing material, such as polymer foam, may applied in an strip around the perimeter of the patch on the upper side and opposite the adhesive material. The collar 62 holds the shape of the patch and provides a press area to press down upon the patch over the adhesive material to make an air tight seal with the primary wound cover. The collar 62 may be peeled away after the patch is set on the cover.

The tube attachment patches shown and described above can be used as part of a combination vacuum assisted wound system, including a primary wound cover, or be applied directly over smaller wounds to apply vacuum therapy. When applied directly over smaller wounds, the adhesive material of the patch provides a conforming air tight seal between the perimeter of the patch and the skin surrounding a wound.

We claim:

1. A tube attachment patch having an adhesive material around its perimeter for attaching the patch in a substantially air-tight seal to a primary wound cover in a vacuum-assisted wound dressing, the patch having a ported vacuum tube fixed to it such that the patch can be oriented on the primary wound cover to locate the tube near an opening in the cover to allow vacuum pressure to be communicated to the wound, the vacuum tube having a ported portion containing a plurality of circumferential flanges and at least one port located in a trough between adjacent flanges.

2. A tube attachment patch having an adhesive material around its perimeter for attaching the patch in a substantially air-tight seal to a primary wound cover in a vacuum-assisted wound dressing, the patch having a ported vacuum tube fixed to it such that the patch can be oriented on the primary wound cover to locate the tube near an opening in the cover to allow vacuum pressure to be communicated to the wound, further comprising a frame fixed to the patch for holding the vacuum tube, the vacuum tube having a ported portion containing a plurality of circumferential flanges and at least one port located in a trough between adjacent flanges.

3. A tube attachment patch as in claim 2, wherein the frame is an enclosure that creates an effective suction chamber around the ported portion of the vacuum tube.

4. A tube attachment patch as in claim 3, the frame having a main body engaging the vacuum tube and a flexible skirt depending downward from the main body to provide a conforming air tight seal between the skirt and wound cover.

5. A vacuum assisted wound dressing comprising:
   a thin-film wound cover adapted to be attached in a substantially air-tight seal to skin surrounding a wound, and having an opening through the cover; and
   a tube attachment patch having an adhesive material around its perimeter for attaching the patch in a substantially air-tight seal to a primary wound cover in a vacuum-assisted wound dressing, the patch having a ported vacuum tube fixed to it such that the patch can be oriented on the primary wound cover to locate the port of the tube near the opening in the cover to allow vacuum pressure to be communicated to the wound; and
   a vacuum tube having one end held in the patch and an opposite end adapted for connection to a source of vacuum pressure the vacuum tube having a ported portion containing a plurality of circumferential flanges and at least one port located in a trough between adjacent flanges.

6. A wound dressing as in claim 5, wherein the frame is an enclosure that creates an effective suction chamber around the ported portion of the vacuum tube.

7. A wound dressing as in claim 6, further comprising the frame having a main body engaging the vacuum tube and a flexible skirt depending downward from the main body to provide a conforming air tight seal between the skirt and wound cover.

8. A patch for applying suction to a wound, comprising:
   a cover comprising a sheet comprising a bottom surface defining a wound side of the sheet and a top surface defining a non-wound side of said sheet, said cover comprising a flexible film adapted to be conformable to anatomical surfaces;
   an opening in said cover;
   a seal for sealing the patch over the wound in a substantially airtight manner, said seal comprising adhesive on the bottom surface of said cover, said adhesive securing the patch over the wound;
   a conduit comprising an interior, an exterior, a proximal end and a distal end, said conduit further comprising a proximal opening in a proximal region of said conduit, and a distal opening, said distal opening being adapted for connection to a source of suction, wherein said proximal end of said conduit is disposed on said non-wound side of said sheet and said distal end of said conduit is disposed away from said sheet, wherein said proximal region of said conduit lies substantially flat over said wound when said patch is secured over said wound;

said exterior of said conduit connected to said top surface of said sheet such that said proximal region of said conduit with said proximal opening is maintained in a substantially non-perpendicular orientation to said sheet;

said interior of said conduit open to said wound via said proximal opening in said conduit and said opening in said cover such that when the patch is sealingly secured over the wound and connected to the source of suction, the wound is maintained at a reduced pressure;

said patch comprising a peel-off layer releasably attached to said adhesive for protecting said adhesive until the patch is applied over the wound;

a collar releasably attached to said film, said collar supporting said film after removal of said peel-off layer and during application of said patch;

said collar being configured for removal after application of said patch; and said patch remaining sealed over said wound after removal of said collar.

9. The patch of claim 8, wherein said film is vapor permeable while still allowing the wound to be maintained at a reduced pressure.

* * * * *

UNITED STATES PATENT AND TRADEMARK OFFICE
CERTIFICATE OF CORRECTION

PATENT NO.       : 7,485,112 B2                                                Page 1 of 1
APPLICATION NO.  : 11/181128
DATED            : February 3, 2009
INVENTOR(S)      : John Karpowicz et al.

It is certified that error appears in the above-identified patent and that said Letters Patent is hereby corrected as shown below:

Title page, item [75] "Inventors:" and after "Christopher L.", please delete "Radle" and add -- Radl -- in its place.

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,485,112 B2
APPLICATION NO.    : 11/181128
DATED              : February 3, 2009
INVENTOR(S)        : John Karpowicz et al.

It is certified that error appears in the above-identified patent and that said Letters Patent is hereby corrected as shown below:

Title page, item [75], under the heading "Inventors:", before "Wynnewood,"

please delete "Klock" and add -- Klocek -- in its place.

Signed and Sealed this

Eighth Day of December, 2009

David J. Kappos
*Director of the United States Patent and Trademark Office*